United States Patent [19]

Plueddemann

[11] 4,093,641

[45] June 6, 1978

[54] PREPARATION OF SILYLALKYL ESTERS OF PHOSPHORUS

[75] Inventor: Edwin P. Plueddemann, Midland, Mich.

[73] Assignee: Dow Corning Corporation, Midland, Mich.

[21] Appl. No.: 836,451

[22] Filed: Sep. 26, 1977

[51] Int. Cl.² ............................................... C07F 7/08
[52] U.S. Cl. ............................................ 260/448.2 E
[58] Field of Search ................................ 260/448.2 E

[56] References Cited

U.S. PATENT DOCUMENTS

| | | | |
|---|---|---|---|
| 2,843,615 | 7/1958 | Linville | 260/448.2 E X |
| 2,995,594 | 8/1961 | Fekete | 260/448.2 E X |
| 2,996,530 | 8/1961 | Fekete | 260/448.2 E X |
| 3,122,581 | 2/1964 | Pike | 260/448.2 E X |

*Primary Examiner*—Paul F. Shaver
*Attorney, Agent, or Firm*—Robert L. McKellar

[57] ABSTRACT

What is disclosed is a novel method of preparing silylalkyl esters of phosphorus using amines or phosphines, which are capable of forming onium compounds with the reactants, as catalysts. They are useful as flame retardant additives and lubricants on metals and textiles.

11 Claims, No Drawings

PREPARATION OF SILYLALKYL ESTERS OF PHOSPHORUS

BACKGROUND

Silylalkyl esters of phosphorus are not new. There are many such materials reported in the chemical literature and their preparations are described in patents and chemical journals.

Such preparative methods are essentially inadequate for the full scale commercial production of these esters as the methods generally result in low yields and uneconomical energy consumption.

For example, one method is described for preparing such esters by the addition of $(C_2H_5O)_3SiH$ to unsaturated phosphites e.g.

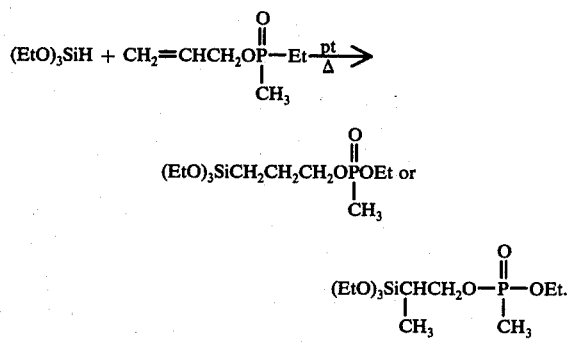

This work was reported by E. F. Petukhova et al. Zh. Obsch. Khim., 1970, 40,(3); 606 CA 73 25569 (1970), and the best yield was 47.4%.

Chloromethylsilanes reacted with sodium diethylthiophosphate was reported to give thiophosphate esters according to the scheme

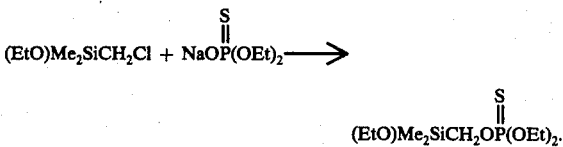

Again, yields were low and the scheme requires the removal of the NaCl solids. [F. Feher and A. Blumke, Ber 90 No. 9 1934 (1957)].

Further, Hewins, et al. has disclosed the preparation of silyl phosphorus esters in C.A. 71, 102318t, from the reaction of

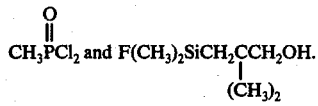

In an early patent, U.S. Pat. No. 2,612,514, Plueddemann disclosed the preparation of higher organic esters of relatively strong acids using amine catalysts. Such reactions did not involve silicon compounds nor were the yields more than moderate.

The above mentioned patent does not disclose or make obvious the instant invention in view of the fact that those skilled in the art would not expect that a haloalkylsilane would react with the methyl ester of phosphorus with such speed and without materially affecting the labile groups on silicon. It is believed that the silicon atom of the haloalkyl or haloaryl silane activates the halogen atom and thereby causes the faster reaction.

It has now been demonstrated that silylalkyl esters of phosphorus can be prepared quickly and in greater yields than has previously been possible.

THE INVENTION

The invention, which will be described in greater detail herein, consists of the discovery that silylalkyl esters of phosphorus can be prepared from a variety of silicon compounds and the methyl esters of phosphorus using amines and phosphines, which are capable of forming onium compounds with the reactants, as catalysts.

Such a preparation results in higher yields of the silylalkyl esters of phosphorus.

Considering the invention in its broadest aspects, it consists of (I) contacting and reacting silanes of the general formula (i) $R_3SiR'X$ or siloxanes of the general formula (ii) $Me_3SiO(Me_2SiO)_n(XR'MeSiO)_mSiMe_3$ or (iii) oligomers of the general formula $(XR'Me_2Si)_2O(-Me_2SiO)_n$ with phosphorus compounds having the general formula

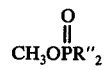

at a temperature in the range of 100° C. to 300° C. in the presence of amines or phosphines capable of forming onium compounds with the reactants, for a period of time sufficient to remove all by-produced organic halide, and then (II) subjecting the resulting reaction mixture to a reduced pressure and an elevated temperature to remove undesired low boiling materials and (III) thereafter recovering the silylalkyl esters of phosphorus, wherein R is an alkyl group, aryl group, alkoxy group containing 1–4 carbon atoms, an R'X group or a siloxy group; X is chlorine, bromine or iodine; $m$ is a positive integer; $n$ is 0 or a positive integer; Me is methyl; R' is a divalent alkyl or aralkyl radical; R" is methyl, ethyl, phenyl, halobenzyl or -OR''' wherein R''' is methyl or phenyl.

This particular catalytic situation allows the preparation of silylalkyl phosphorus esters that also contain hydrolyzable groups on the silicon atoms. It is therefore an especially important invention. It is important to note that the only critical aspect of the amine or phosphine catalysts is that they must be able to form an onium compound. It does not appear at this time that there is any criticality between previously prepared onium compounds and those that are formed in situ in the reacting mixture.

It is believed, but the inventor does not wish to be held to such a theory, that the reactants form mixed onium salts with the catalysts which decompose to silylalkyl esters and organic halides with regeneration of the catalyst. The desired reaction goes to completion through removal of the organic halide by volatilization.

Examples of amine catalysts operable in this invention include tertiary amines such as triethylamine, triethanolamine, tributylamine and the like. Also, when primary or secondary amines are used in this invention, they must be of the type that perform in the same manner as the tertiary amines, that is, in the reaction mass, they react with the alkyl or aralkyl chlorides to give quaternary salts.

Examples of phosphine catalysts include tributylphosphine, dibutylmonomethylphosphine and the like.

The reaction of the instant invention is sometimes enhanced by the addition of other materials which promote the reaction e.g. the use of a small amount of $Na_2CO_3$ with tributylphosphine.

The amount of catalyst required for this reaction depends on the reactants employed. Generally, from 0.1 to 3.0 weight percent based on the weight of the reactants is utilized.

The silanes (i) having the general formula $R_3SiR'X$ are readily obtained commercially and therefore no extended recitation on their preparation is required here.

R in these silanes represents alkyl groups, aryl groups, alkoxy groups containing 1–4 carbon atoms, siloxy groups or R'X groups which are attached directly to a silicon atom. The silanes must have at least one R'X group attached to the silicon atom. The R groups can be all of the same kind of R groups such as $(CH_3O)_3$ or the R groups can be a mixture of groups as set forth above such as, for example, $$ClCH_2CH_2CH_2\underset{(OCH_3)_2}{\overset{|}{Si}}-$$

Examples of alkyl groups are those having 1–6 carbon atoms such as $CH_3-$, $CH_3CH_2-$,

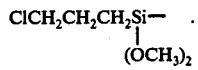

and $CH_3(CH_2)_3$. Examples where R is an aryl group include $C_6H_5$ and $C_6H_4CH_2$. Examples of R as alkoxy groups includes $CH_3O$, $CH_3CH_2O$, and $CH_3(CH_2)_3O$. Examples of R as a siloxy group include $Me_3SiO$, $ClCH_2Me_2SiO$ and $\phi Me_2SiO$.

R' is a divalent alkyl or aralkyl group and acts as a bridging group between the silicon atom and the X group. Generally, it is preferred that such a group be from 1–10 carbons in number. The R' can be for example an alkylene group such as methylene, ethylene, propylene or butylene. It can be an aralkylene such as

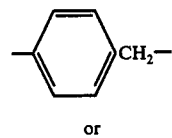

or

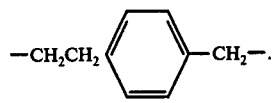

At the present time, there does not appear to be any critical feature of this bridging group as long as it is 10 or less carbons in structure and the halogen is on a primary or secondary aliphatic position.

The X represents a halogen atom which can be chlorine, bromine or iodine. It is preferred that X be chlorine or bromine because such iodo derivatives are not readily available in commerce.

The siloxanes (ii) having the general formula $Me_3SiO(Me_2SiO)_n(XR'MeSiO)_3$ are also readily obtained commercially and their preparation need not be explained here. Suffice it to say that such siloxanes, where Me is the methyl group, are obtained by simple hydrolysis of the corresponding chloro or alkoxy silanes. Such siloxanes for purposes of this invention must contain at least one $(XR'MeSiO)$ unit in order to be useful in this invention. The value of $n$ is not critical but it should be low enough so that the material has a low enough viscosity to be easily handled. $m$ is at least 1 and can be as high as 40–50. For purposes of this invention, however, it is preferred that $m$ not exceed about 12. R' in this formula has the same meaning as R' has in the silane (i) above.

The oligomers (iii) having the general formula $(XR'Me_2Si)_2O(Me_2SiO)_n$ are readily obtained by the cohydrolysis of the corresponding chloro or alkoxy silanes by conventional techniques and methods. As can be observed from the formula, these materials are linear in nature and are low molecular weight. The value of $n$ in this formula does not generally exceed about 10. The meaning of R' in this formula is the same as R' above.

The phosphorous compounds which form the second type of reactant in this invention are the methyl esters of phosphorus and have the formula $$CH_3O\overset{\overset{O}{\|}}{P}R''_2.$$

As can be observed from the formula $$CH_3O\overset{\overset{O}{\|}}{P}R''_2,$$

there must be present at least one methoxy group on phosphorus i.e.

$$CH_3O\overset{\overset{O}{\|}}{\underset{|}{P}}-.$$

Such methyl esters are readily obtainable commercially and those preferred for this invention are those where R'' is methyl, phenyl, benzyl, halobenzyl or -OR''' where R''' is methyl or phenyl.

Specific examples of such materials include

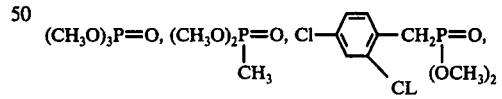

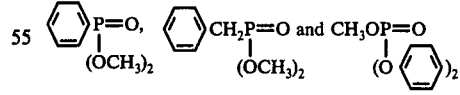

The ratio of reactants, that is, the ratio of either (i), (ii), (iii) to the phosphorus compound is dependent upon what the materials are being used for. Generally, a stoichiometric ratio plus up to 100% of the reactive materials is employed. For example, if the material is to be used in an application where the mono-silylalkyl ester is desired from a dimethoxy or trimethoxy phosphorus compound, a relatively large excess of the phosphorus ester would be present to decrease the formation of di- or tri-silylalkyl phosphorus esters; for example,

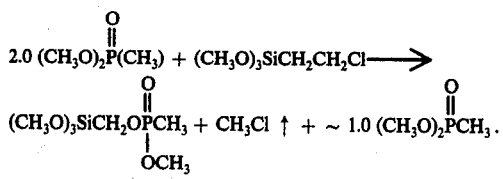

Sometimes, large excesses of the other reactant may be required.

For example, if one wished to prepare {(CH₃O)₃-SiCH₃CH₂CH₂O}₃P=O rather than

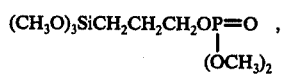

then the stoichiometry would have to change to accomodate this.

In the first case, at least 3 moles of (CH₃O)₃SiCH₂CH₂Cl would be required to react with one mole of (CH₃O)₃P=O while in the second case only 1 mole of (CH₃O)₃SiCH₂CH₂CH₂Cl for 1 mole of (CH₃O)₃P=O would be required.

Generally, no solvent is required for this reaction but it is believed that small quantities of solvents could be used without detrimental effect on the invention.

The reaction is dependent upon the use of certain amines or phosphines as catalysts. These catalysts must be capable of forming onium compounds with the reactants. By "onium", for purposes of this invention, we mean that the amine and phosphines must be capable of forming ions having a positive charge such as phosphonium and ammonium ions.

This invention is to be differentiated from the Arbusov reaction wherein chloroalkylsilicon compounds are merely heated with methyl phosphite esters i.e.

without the benefit of a catalyst. (Cotton and Wilkinson, "Advanced Inorganic Chemistry", 2nd edition, page 512).

The inventive reaction is carried out by contacting any of the reactants (i), (ii) or (iii) with the phosphorus compound in the presence of the amine or phosphine catalyst and heating. The heating serves to help remove the by-produced organic halide.

The general reaction is believed to be

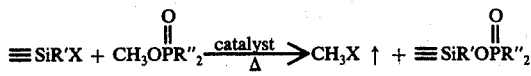

The temperature at which the reaction is conducted is not narrowly critical and depends mainly on the boiling point of the by-produced CH₃X. A preferred range is 100° C. to 300° C. The period of time required for the reaction is dependent on the amount of time it takes to remove the by-produced CH₃X and this time normally ranges from 20 minutes to several hours depending on the size of the reaction being run and the reactants used.

When all of the by-produced CH₃X has been removed and the reaction is essentially complete, the reaction mixture is then stripped, preferably under reduced pressure, to remove excess reactants and other low boiling materials. The product can be used at this stage or it can be further purified by distillation.

The products are clear, almost colorless, liquids which do not generally require filtration. These materials have utility as lubricants on metal and textiles and as flame retardant additives.

Now, so that those skilled in the art can better understand the invention, the examples below are presented. Whenever used herein, φ means phenyl, Me means methyl and Et means ethyl.

MONOMERIC SILYLALKYL PHOSPHATES

EXAMPLE 1

A mixture of 14.2 g $(CH_3O)_3P=O$ (0.1 mole), 100 g. $(CH_3O)_3SiCH_2CH_2CH_2Cl$ (0.5 mole), and 2 g. $(CH_3O)_3SiCH_2CH_2CH_2—NHCH_3$ (amine catalyst) was warmed from 148° to 198° over 30 minutes while measuring 7.5 l. of evolved gas (mainly CH₃Cl by mass spec analysis). The product was stripped to 150° at 1 mm. to recover 60 g. of crude {(CH₃O)₃SiCH₂CH₂CH₂O}₃P=O.

The crude product was distilled from 0.5 g. Na₂CO₃ to recover 46 g., b. 200–220 1 mm., dens 25° 1.157, $n_D^{25}$ 1.4345 analyzing 13.5% Si and 6.1% P (theory for {CH₃O)₃SiCH₂CH₂CH₂O}₃P=O = 14.4% Si, 5.31% P.

In contrast to this phosphate ester, a comparable silylalkyl phosphonate prepared by the Arbusov reaction of $(CH_3O)_3SiCH_2CH_2CH_2Cl$ and $(CH_3O)_3P \xrightarrow{\Delta} (CH_3O)_3SiCH_2CH_2CH_2—P=O(OCH_3)_2 + CH_3Cl$ gave a crude product that decomposed and rearranged extensively during preparation and attempted distillation so that the pure product could not be isolated.

EXAMPLE 2

Monomeric Silylalkyl Phosphonates

A mixture of 400 g. $(CH_3O)_3SiCH_2CH_2CH_2Cl$ (2 mols) and 250 g. $CH_3PO(OCH_3)_2$ (2 mols) with 2 g. benzyl dimethylamine catalyst was warmed from 100° to 182° during 1 hour while measuring 45 liters of evolved gas (mainly CH₃Cl by mass spec. analysis).

The crude product was distilled from 1 g. Na₂CO₃ to recover 200 g. lights (mainly unreacted starting materials), I. 225 g. b, 110°–150°, dens ²⁵ 1.1400, $n_D^{25}$ 1.4298 almost pure

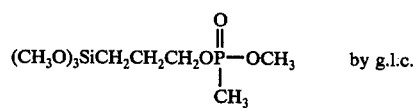

II. 205 g. b, 150°–220°, predominately

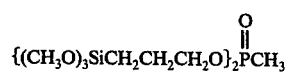

with some I. and 15 g. residue.

EXAMPLE 3

A mixture of 134.5 g.

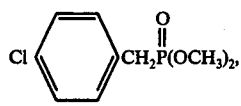

(0.5 mol) and 100 g. (CH₃O)₃SiCH₂CH₂CH₂Cl (0.5 mole) with 2 g. benzyldimethylamine catalyst was warmed from 135°–200° during six hours while measuring 14.1 l. of evolved gas. The residue was a clear oil $n_D^{25}$ 1.5067 that had a proton nuclear magnetic resonance in agreement with the structure

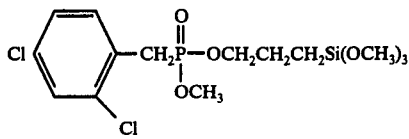

with a small amount of aromatic impurity.

EXAMPLE 4

A mixture of 12.4 g.

(0.2 mol), 29.1 g.

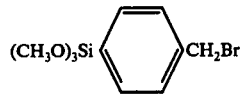

and 1 g. benzyldimethylamine was warmed from 125°–175° during 30 minutes while collecting 2.2 l. of gas that was analyzed by infrared spectroscopy to consist of >90% CH₃Br with 1.7 mol% CH₃OCH₃ and 5.7 mol% CH₃OH. The residue was

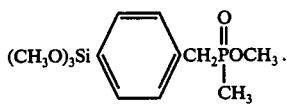

EXAMPLE 5

Polymers with Silylalkyl phosphonates in the polymer Chain

A mixture of 46.2 g.

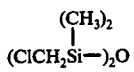

(0.2 mol) and 38 g.

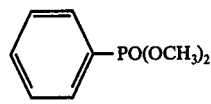

(0.2 mol) with 0.2 g. benzyldimethylamine and 0.1 g. Na₂CO₃ was heated from 175°–300° C during 22 minutes while measuring 9.3 l. of evolved gas. The residue was stripped to 150° at 1 mm Hg pressure to recover 65 g. of clear amber, viscous fluid.

Filter paper was dipped in a 10% toluene solution of the product and dried to remove toluene. Pickup was 60% of the weight of paper. The treated paper could be ignited with difficulty with a flame, but the fire went out as soon as the paper was removed from the flame.

EXAMPLE 6

Similarly 60 g. Cl₂C₆H₃CH₂PO(OCH₃)₂ (0.2 mol) and 46 g.

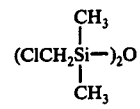

(0.2 mol) with 1 g. benzyldimethylamine heated to 250° gave 6.1 l. of evolved CH₃Cl and 70 g. of a viscous oily fluid of the structure

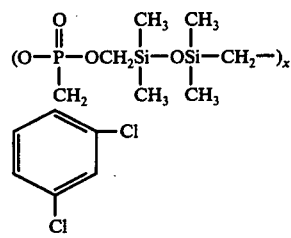

EXAMPLE 7

A mixture of 85 g.

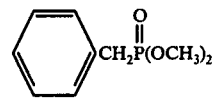

(0.42 mol), 85 g.

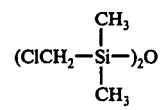

(0.74 mol), 1 g. tributylphosphine and 0.5 g. Na₂CO₃ was heated to 300° C. until 19 l. gas was evolved. The residue was stripped to 150°, mm. to recover a clear viscous fluid analyzing nil - Cl, 10.1% P and 15.7% Si. Theory for

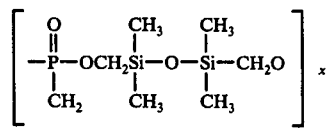

is 9.4% and 16.9% Si. In a 4-ball lubricity test on steel, the above fluid at 167° F withstood a 4 kg. load to a 0.25 mm. scar on the bearings.

EXAMPLE 8

Polysiloxanes with Dangling Silylalkyl Phosphonate (or Phosphate) Groups

A siloxane fluid of the composition $(Me_3SiO)_2(Me_2SiO)_7(MeHSiO)_3$ 100 g = (0.352 equiv. SiH) was added to 60 g. vinylbenzylchloride (40% para and 60% meta mixed isomers) and 15 drops of a 1% Pt solution as chloroplatinic acid in isopropanol at 100°. After a slight exotherm no Si-H remained in the mixture. The product was stripped to 150°, mm., mixed with 124 g.

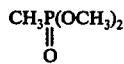

(1 mol) and 1 g. benzyldimethylamine and warmed during 7 hours from 150°–180° while measuring 7.7 liters of evolved gas. The residue was stripped to 150°, mm., to recover 200 g. of clear fluid, dens. $^{25°}$ 1.23 and viscosity at 25° 10,000 cs. This fluid was suitable as a textile lubricant with improved fire retardancy as compared with a comparable poly(dimethylsiloxane).

EXAMPLE 9

Similarly the product from 100 g. siloxane fluid (0.352 eq. SiH) and 60 g. vinylbenzyl chloride was warmed with 132 g. methyl diphenyl phosphate (0.5 mol) and 1 g. benzyldimethylamine was heated from 160° to 220° during 4 hours while measuring 6 liters of evolved gas. The residue was a clear amber, viscous fluid, dens. $^{25°}$ 1.075, viscosity 47 cs. at room temperature comprising a polysiloxane with pendant

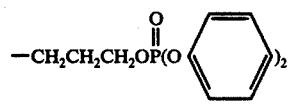

groups having superior fire retardant properties.

EXAMPLE 10

This is a comparison example to show the relative rates of reaction of alkylhalide against a haloalkylsilane.

n-Dodecylchloride (1 chloro-n-dodecane) was compared with $(MeO)_3SiCH_2CH_2CH_2Cl$ for reactivity with

in the presence of benzyldimethylamine catalyst. The by-produced gas that was evolved in each case was measured as an indicia of the amount of reaction that had taken place. The following formulations were prepared.

|  | n - $C_{12}H_{25}Cl$ mw = 205 | $(MeO)_3SiCH_2CH_2CH_2Cl$ mw = 200 |
|---|---|---|
| $MeP(OMe)_2$ | 20.5 gms | 20 gms |
|  | 25.0 gms | 25 gms |
| Benzyl $NMe_2$ | 0.4 gms | 0.4 gms |

| | n-$C_{12}H_{25}Cl$ temp° C | gas | $(MeO)_3SiCH_2CH_2CH_2Cl$ temp° C | gas |
|---|---|---|---|---|
| >1 hr. | 165° | 0 | 135° | 0 |
|  | 178° | 0.22 l | 152° | 0.22 l |
|  | 192° | 1.2 l | 170° | 1.2 l |
|  | 190–195° | 20 min. | 200° | |
|  | reflux | finish |  | finish |

These data indicate that $Cl(CH_2)_3Si(OMe)_3$ react much more readily and completely with methyl esters of phosphorus than does an n-alkyl chloride of comparable molecular weight and boiling point.

EXAMPLE 11

The material of Example 2(I.) was compared to other functional silicones as to their effect upon the limiting oxygen index (LOI) upon carded sateen cotton. LOI is a test which measures the amount of oxygen necessary to support combustion. The lower the LOI, the more flammable is the substance, that is the lower the LOI, the lesser need of $O_2$ to support combustion (ASTM D-2863).

| | The Effect of Various Silicone Finishes Upon The O.I. of 8.5 oz. Carded Sateen Cotton | | | | | | |
|---|---|---|---|---|---|---|---|
| | Measured Cotton Blank LOI is 0.175 LOI at Various Add-On Levels | | | | | | |
| Finish | 0.5% | 1.0% | 2.5% | 5.0% | 10.0% | 20.0% | 25.0% |
| dimethyl/methyl hydrogen copolymer | 0.174 | 0.175 | 0.179 | 0.180 | 0.182 | 0.188 | — |
| $HO(Me_2SiO)_xOH$ | — | 0.176 | 0.175 | 0.175 | 0.177 | 0.184 | — |
| $MeSiO_{3/2}$ gel | — | 0.174 | — | 0.184 | — | 0.189 | — |
| $Me_3SiO(Me_2SiO)_xSiMe_3$ 60,000 cstk. visc. | — | — | 0.180 | — | — | — | — |
| phenylmethyl polysiloxane | — | — | — | 0.178 | 0.179 | 0.183 | — |
| carboxyfunctional polydimethylsiloxane | — | — | 0.178 | 0.181 | 0.183 | 0.183 | — |
| aminofunctional polydimethylsiloxane | — | — | — | 0.189 | 0.192 | — | — |
| $(MeO)_3Si(CH_2)_3OPOCH_3$ / $CH_3$ with O= | 0.183* | 0.184 | 0.187 | 0.193 | 0.207 | 0.233 | 0.246 |

*extrapolated

It can be readily observed that the

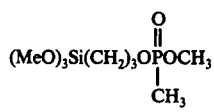

compound has a flame retardant capacity greater than any of the other materials shown.

That which is claimed is:

1. A method of preparing silylalkyl esters of phosphorus which consists of
   (I) contacting and reacting silanes of the general formula
   (i) $R_3SiR'X$ or siloxanes of the general formula
   (ii) $Me_3SiO(Me_2SiO)_n(XR'MeSiO)_mSiMe_3$ or
   (iii) oligomers of the general formula $(XR'Me_2Si)_2O(Me_2SiO)_n$ with phosphorus compounds having the general formula

at a temperature in the range of 100° C. to 300° C. in the presence of amines or phosphines capable of forming onium compounds with the reactants, for a period of time sufficient to remove all by-produced organic halide, and then
   (II) subjecting the resulting reaction mixture to a reduced pressure and an elevated temperature to remove undesired low boiling materials and
   (III) thereafter recovering the silylalkyl ester of phosphorus, wherein
   R is an alkyl group, aryl group, alkoxy group containing 1–4 carbon atoms, an R'X group or a siloxy group;
   X is chlorine, bromine or iodine;
   m is a positive integer;
   n is 0 or a positive integer;
   Me is methyl;
   R' is a divalent alkyl or aralkyl radical;
   R" is methyl, ethyl, phenyl, halobenzyl or —OR'" wherein R'" is methyl or phenyl.

2. The method of claim 1 wherein an amine is present during the reaction, $R_3$ is $(CH_3O)_3$, X is chlorine, R' is an alkylene group.

3. The method of claim 1 wherein a phosphine is present during the reaction, $R_3$ is $(CH_3O)_3$, X is chlorine and R' is an alkylene group.

4. The method of claim 1 wherein an amine is present during the reaction, $R_3$ is $(CH_3O)_3$, X is bromine and R' is an alkylene group.

5. The method of claim 1 wherein the phosphorus compound has the formula

and at least one R' is $CH_3O$.

6. The method of claim 1 wherein the phosphorus compound has the formula

and R" is phenoxy.

7. The method of claim 2 wherein the amine present during the reaction is benzyldimethylamine, $R_3$ is $(CH_3O)_3$, X is chlorine and R' is $—CH_2CH_2CH_2—$.

8. The method of claim 2 wherein the amine present during the reaction is $(CH_3O)_3SiCH_2CH_2CH_2NHCH_3$, $R_3$ is $(CH_3O)_3$, X is chlorine and R' is $—CH_2CH_2CH_2—$.

9. The method of claim 3 wherein the phosphine present during the reaction is tributylphosphine, $R_3$ is $(CH_3O)_3$, X is chlorine and R' is $—CH_2CH_2CH_2—$.

10. The method of claim 4 wherein the amine present during the reaction is benzyldimethylamine, $R_3$ is $(CH_3O)_3$, X is bromine and R' is

11. The method of claim 5 wherein both R" are $CH_3O$.

* * * * *

UNITED STATES PATENT AND TRADEMARK OFFICE
CERTIFICATE OF CORRECTION

PATENT NO. : 4,093,641
DATED : June 6, 1978
INVENTOR(S) : Edwin P. Plueddemann

It is certified that error appears in the above-identified patent and that said Letters Patent are hereby corrected as shown below:

In Column 3, line 67; the formula reading "$O(Me_2SiO)_n(XR'MeSiO)_3$" should read "$O(Me_2SiO)_n(XR'MeSiO)_m SiMe_3$".

In Column 6, line 20; the formula reading "$SiCH_2CH_2CH_2-NHCH_3$" should read "$SiCH_2CH_2CH_2NHCH_3$".

In Column 6, line 34; the formula reading "$_3O)_3SiCH_2CH_2CH_2-P=O(OCH_3)_2 + CH_3Cl$" should read "$O)_3SiCH_2CH_2CH_2P=O(OCH_3)_2 + CH_3Cl$".

In Column 7, line 7; the word reading "mole)" should read "mol)".

In Column 7, line 30; the line reading "(0.2 mol), 29.1 g." should read "(0.1 mol), 29.1 g.".

UNITED STATES PATENT AND TRADEMARK OFFICE
CERTIFICATE OF CORRECTION

PATENT NO. : 4,093,641
DATED : June 6, 1978
INVENTOR(S) : Edwin P. Plueddemann

It is certified that error appears in the above-identified patent and that said Letters Patent are hereby corrected as shown below:

In Column 10, line 26; the word "finish" under the column heading reading "$(MeO)_3SiCH_2CH_2CH_2Cl$" should be moved up one line so it is horizontally across from "200°". In other words, "200°" and "finish" should be on the same line.

Signed and Sealed this

Tenth Day of July 1984

[SEAL]

Attest:

GERALD J. MOSSINGHOFF

Attesting Officer

Commissioner of Patents and Trademarks